United States Patent
Grass et al.

(10) Patent No.: US 9,217,351 B2
(45) Date of Patent: Dec. 22, 2015

(54) METHOD AND DEVICE FOR OPERATING AN SCR SYSTEM

(75) Inventors: Philippe Grass, Regensburg (DE); Denny Schädlich, Neustadt (DE)

(73) Assignee: Continental Automotive GmbH, Hannover (DE)

( * ) Notice: Subject to any disclaimer, the term of this patent is extended or adjusted under 35 U.S.C. 154(b) by 67 days.

(21) Appl. No.: 14/119,085

(22) PCT Filed: May 21, 2012

(86) PCT No.: PCT/EP2012/059322
§ 371 (c)(1),
(2), (4) Date: Nov. 20, 2013

(87) PCT Pub. No.: WO2012/160009
PCT Pub. Date: Nov. 29, 2012

(65) Prior Publication Data
US 2014/0096511 A1    Apr. 10, 2014

(30) Foreign Application Priority Data
May 26, 2011   (DE) .......................... 10 2011 103 272

(51) Int. Cl.
*F01N 3/20* (2006.01)
*F01N 11/00* (2006.01)
(Continued)

(52) U.S. Cl.
CPC .............. *F01N 3/2066* (2013.01); *F01N 11/00* (2013.01); *G01N 29/024* (2013.01); *G01N 29/07* (2013.01);
(Continued)

(58) Field of Classification Search
CPC . F01N 11/00; F01N 2560/12; F01N 2610/10; F01N 2900/1811; F01N 2900/1818; G01N 27/14; G01N 29/024; G01N 29/036; G01N 29/07; G01N 29/326
See application file for complete search history.

(56) References Cited

U.S. PATENT DOCUMENTS

2003/0236635 A1    12/2003  Priev et al.
2009/0301059 A1*  12/2009  Toshioka et al. ................ 60/277
(Continued)

FOREIGN PATENT DOCUMENTS

CN    100465632    3/2009
CN    101548077    9/2009
(Continued)

OTHER PUBLICATIONS

Prof. Dr.-Ing. Jörg Hoffmann; "Handbuch der Messtechnik"; 3th revised edition; 2007; cover sheet (2 pages) and pp. 248-249; ISBN 978-3-446-40750-3; Carl Hanser Verlag; Munich; Germany.
(Continued)

*Primary Examiner* — Kenneth Bomberg
*Assistant Examiner* — Jonathan Matthias
(74) *Attorney, Agent, or Firm* — Cozen O'Connor

(57) ABSTRACT

A method for operating a selective catalytic reduction (SCR) system having a urea solution supply and an ultrasound based urea concentration sensor, the measurement signal of the urea concentration sensor being representative of a propagation time of an ultrasonic pulse along a predefined path length in a fluid of the urea solution supply includes: heating at least the fluid in a detection region of the urea concentration sensor from a predefined first temperature to a predefined second temperature; during the heating, detecting the measurement signal at at least a third and fourth temperature, and in each case determining a raw concentration characteristic value as a function of the respective measurement signal, which raw concentration characteristic value is representative of the propagation time of the ultrasonic pulse; and determining a concentration characteristic value, representative of a concentration of urea in the fluid, as a function of the raw concentration characteristic values.

6 Claims, 2 Drawing Sheets

(51) Int. Cl.
*G01N 29/024* (2006.01)
*G01N 29/07* (2006.01)
*G01N 29/32* (2006.01)

(52) U.S. Cl.
CPC .......... *G01N 29/326* (2013.01); *F01N 2550/05* (2013.01); *F01N 2560/026* (2013.01); *F01N 2560/12* (2013.01); *F01N 2560/20* (2013.01); *F01N 2610/10* (2013.01); *F01N 2900/1814* (2013.01); *F01N 2900/1818* (2013.01); *G01N 2291/0224* (2013.01); *G01N 2291/02809* (2013.01); *Y02T 10/24* (2013.01); *Y02T 10/47* (2013.01)

(56) References Cited

U.S. PATENT DOCUMENTS

| | | | | |
|---|---|---|---|---|
| 2010/0242621 | A1* | 9/2010 | Estrada et al. | 73/861.27 |
| 2012/0031082 | A1 | 2/2012 | Gismervik | |
| 2012/0118059 | A1* | 5/2012 | Reimer et al. | 73/290 V |
| 2013/0167622 | A1* | 7/2013 | Frivik | 73/61.46 |

FOREIGN PATENT DOCUMENTS

| | | |
|---|---|---|
| CN | 101988409 | 3/2011 |
| DE | 10 2006 013 263 A1 | 9/2007 |
| DE | 10 2009 040 111 A1 | 3/2011 |
| EP | 1538437 | 6/2005 |
| EP | 2 343 548 A2 | 7/2011 |
| KR | 20100069761 | 6/2010 |
| WO | WO 02/04916 A2 | 1/2002 |
| WO | WO 2007/104779 A2 | 9/2007 |
| WO | WO 2010/110669 A1 | 9/2010 |
| WO | WO 2010/110839 | 9/2010 |

OTHER PUBLICATIONS

Qian et al. "Optimization of Urea-SCR Exhaust Pipe Layout and Catalyst Development", Jun. 2010, p. 100.

Gabrielsson, "Urea-SCR in Automotive Applications", Apr. 2004, pp. 177-184.

* cited by examiner

METHOD AND DEVICE FOR OPERATING AN SCR SYSTEM

CROSS-REFERENCE TO RELATED APPLICATIONS

This is a U.S. national stage of application No. PCT/EP2012/059322, filed on 21 May 2012, which claims priority to the German Application No. 10 2011 103 272.3, filed 26 May 2011, the content of both incorporated herein by reference.

BACKGROUND OF THE INVENTION

1. Field of the Invention

The invention relates to a method and to a device for operating an SCR system in an internal combustion engine.

2. Related Art

Within the scope of strict regulations relating to the emissions of pollutants emitted by motor vehicles, an important measure is to keep low the emissions of pollutants that are produced during the combustion of the air/fuel mixture in the respective cylinders of the internal combustion engine.

A further measure is also to use exhaust gas post-treatment systems that convert the emissions of pollutants generated during the combustion process of the air/fuel mixture in the respective cylinder into non-damaging substances. For this purpose, exhaust gas catalytic converters are used that convert carbon monoxide, hydrocarbons and also nitrogen oxides into non-damaging substances. In particular in the context of diesel internal combustion engines, for example particle filters are used and also SCR (selective catalytic reduction) catalytic converters are used. Such SCR catalytic converters selectively reduce the nitrogen oxides. This means that, in particular, nitrogen oxides such as NO, $NO_2$ are reduced, while undesired secondary reactions are avoided. Ammonia ($NH_3$) is necessary for this reaction.

In the case of SCR systems comprising an SCR catalytic converter, in the field of motor vehicles a reducing agent is metered into the exhaust gas train. Odorless urea is used as the reducing agent since ammonia in its pure form has a high level of toxicity and is also flammable. An aqueous urea solution, which is also marketed by the brand name AdBlue® is made available as the reducing agent. The reducing agent is generally stored in a separate tank in the vehicle.

The consumption of the reducing agent is between 2 to approximately 8% of the fuel, in particular of the diesel fuel.

In order to reduce the nitrogen oxide emissions as much as possible it is important that the reducing agent be metered with the correct ratio. If the metering is too low, the efficiency of the reduction in the nitrogen oxide drops. If the portion of urea is too high, the ammonia which is formed therefrom may to a certain extent not react with the nitrogen oxides.

DE 10 2006 013 263 A1 discloses a method for determining the concentration of a component of a fluid provided for exhaust gas purification, in which method a concentration of the component in the fluid is determined by means of a measurement of the speed of sound in the fluid.

WO 2007/104779 A2 discloses a method for checking a composition of an ammonia solution, in which method a reference temperature profile is recorded and a test temperature profile is compared with the reference temperature profile.

SUMMARY OF THE INVENTION

An object of the invention is to provide a method and a device for operating an SCR system which respectively permit the concentration of urea to be determined reliably.

The object is achieved by a method and a corresponding device for operating an SCR system having a urea solution supply and having an ultrasound-based urea concentration sensor, the measurement signal of which is representative of a propagation time of an ultrasonic pulse along a predefined path length in a fluid of the urea solution supply.

At least the fluid in a detection region of the urea concentration sensor is heated from a first temperature to a predefined second temperature. During the heating, the measurement signal is detected at at least a third temperature and a fourth temperature which is different from the third temperature, and in each case a raw concentration characteristic value is determined as a function of the respective measurement signal, which value is representative of the propagation time of the ultrasonic pulse. For example, the third temperature can approximately correspond to the first temperature, and the fourth temperature can approximately correspond to the second temperature.

A concentration characteristic value, which is representative of a concentration of urea in the fluid, is determined as a function of the raw concentration characteristic values.

In this way, use is made of the realization that when there are changes in temperature, the propagation time of the ultrasonic pulse along the predefined path length in the fluid changes in a way characteristic of the respective actual concentration of urea in the fluid. In this way, the concentration of urea can therefore be determined very reliably. In particular, faulty interpretations of the measurement result are thus correspondingly avoided on the basis of identical speeds of sound in the case of a single predefined temperature of two different solutions with different urea content. In this way, it is therefore possible reliably to detect, for example, when the fluid does not have the predefined concentration of urea, which is, for example, 32.5% in the case of AdBlue®. It is therefore possible, in particular, to detect dilution with water or else, if appropriate an increased concentration if the fluid contains further undesired components such as, for example, a coolant or salt water.

Corresponding measures, such as, for example, a warning message to the driver of the vehicle or else an entry in a fault memory or, if appropriate, adaptation of the metered quantity which is metered into the exhaust gas, can then be initiated as a function of the concentration characteristic value.

According to one advantageous aspect, a gradient is determined as a function of the raw concentration characteristic values and the assigned temperatures, and the concentration characteristic value is determined as a function of the gradient. In this way, the concentration characteristic value can be determined by computing technology in a particularly favorable and also reliable way.

According to one further advantageous aspect the urea concentration sensor is additionally designed and arranged to detect a fluid filling level in a fluid tank of the urea solution supply. In this way, a single sensor can be used both to detect the fluid filling level in the fluid tank and to determine the concentration characteristic value.

According to a further advantageous aspect, the determination of the concentration characteristic value is carried out in response to detection that a predefined threshold value of the nitrogen oxide concentration in an exhaust gas downstream of an SCR catalytic converter of the SCR system is exceeded. In this way, the determination of the concentration characteristic value can be carried out in a very selective fashion and limited, in particular, to situations in which such determination is particularly necessary with a view to minimizing nitrogen oxide emissions. In this context, a contribution is also made to keeping the energy requirement of the SCR system as low as possible since the heating and corresponding detection by means of the urea concentration sensor must only take place in a very selective way.

According to a further advantageous refinement, the difference between the first and second temperatures is greater than a measuring inaccuracy of the urea concentration sensor. In this context, the difference can particularly advantageously be approximately at least 10° C. This contributes to particularly reliable determination of the concentration characteristic value.

According to a further advantageous refinement, the urea concentration sensor is arranged in such a way that the ultrasonic pulse is emitted into a feed line of the urea solution supply. In this way, the required heating energy to heat the urea solution can, for example, also be kept particularly low since only the quantity of fluid flowing through in the feed line has to be correspondingly heated.

BRIEF DESCRIPTION OF THE DRAWINGS

Exemplary embodiments of the invention are explained in more detail below with reference to the schematic drawings, in which.

DETAILED DESCRIPTION OF THE PRESENTLY PREFERRED EMBODIMENTS

Figure 1:
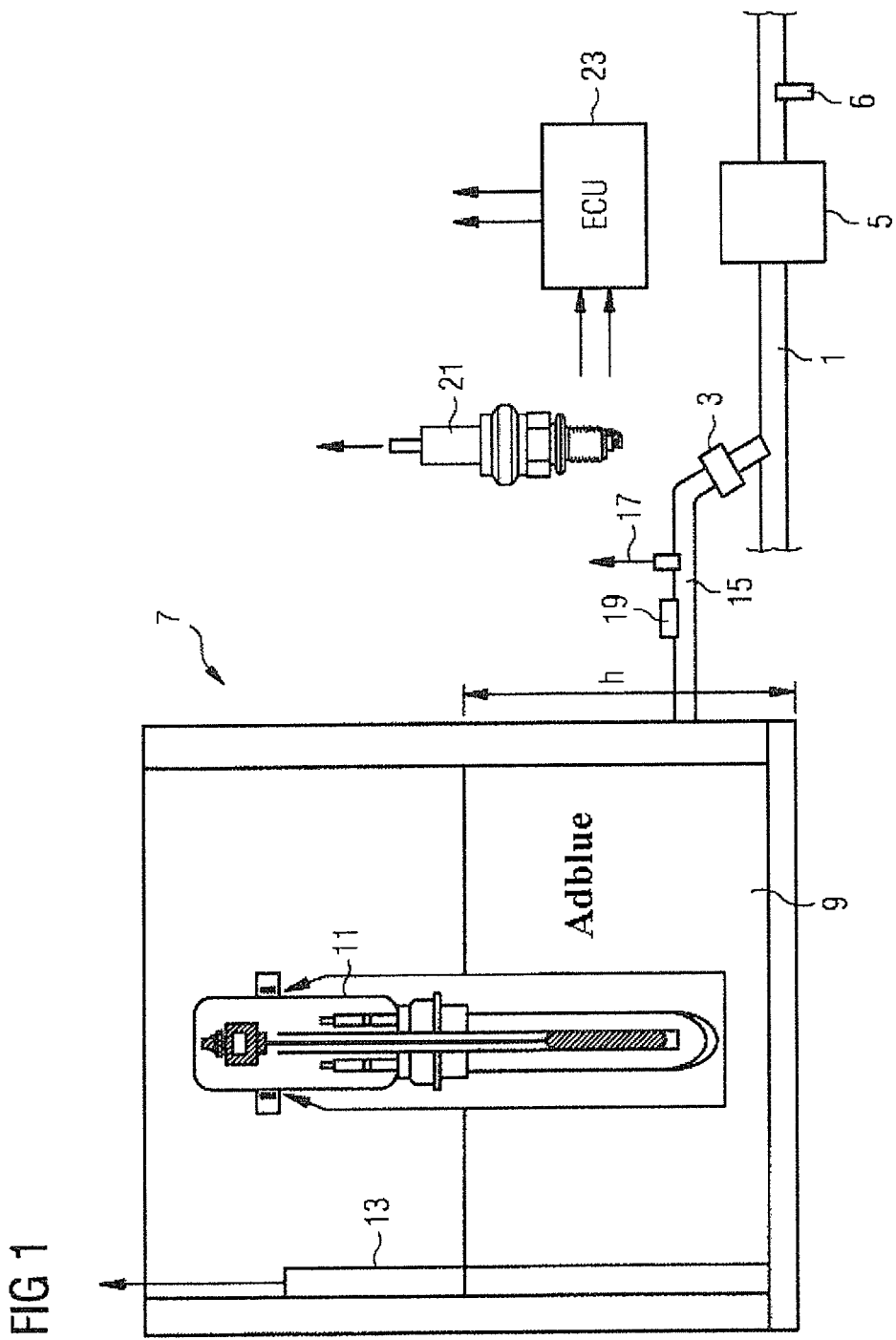
FIG. 1 shows an SCR system with a control device 23.

An SCR system is assigned to an internal combustion engine and is assigned, in particular, to the exhaust gas train of the internal combustion engine. The internal combustion engine is embodied, in particular, as a diesel internal combustion engine and has in its exhaust gas section an exhaust gas duct 1 (FIG. 1) which is arranged downstream of corresponding cylinders of the internal combustion engine. As a result, exhaust gas from the corresponding cylinders reaches the exhaust gas duct 1 directly or indirectly.

For example, an exhaust gas catalytic converter can be arranged upstream of the exhaust gas duct 1, which is illustrated in the figure, and/or a turbine of an exhaust gas turbocharger can be arranged upstream of the exhaust gas duct 1. Optionally, a particle filter can also be arranged upstream of the illustrated exhaust gas duct 1. Furthermore, one or more sensors can also be arranged upstream of the illustrated exhaust gas duct 1.

A metering unit 3 is arranged in the exhaust gas duct 1, specifically in such a way that it is configured to meter fluid 9, containing urea, into the exhaust gas duct 1. Arranged downstream of the metering unit 3 is an SCR catalytic converter 5 in the exhaust gas duct 1. The SCR catalytic converter 5 is designed to carry out a reduction of nitrogen oxides to form water and nitrogen with the aid of ammonia which is obtained from the urea.

Further sensors, such as a nitrogen oxide sensor or an exhaust gas temperature sensor, can be arranged downstream and/or upstream of the SCR catalytic converter 5. For example, in the figure the nitrogen oxide sensor 6 is arranged downstream of the SCR catalytic converter.

The SCR system also comprises a fluid tank 7, which is filled with fluid that should comprise a predefined proportion of urea. The fluid tank 7 is coupled hydraulically to the metering unit 3 in order to supply the metering unit 3 with fluid from the fluid tank 7. A supply of urea solution also comprises a feed line 15 in addition to the fluid tank 7.

A filling level of the fluid 9 in the fluid tank 7 is denoted by h. A tank heating element 11 is arranged in the fluid tank 7 in order to feed thermal energy to the fluid 9 which is contained in the fluid tank 7. In addition, a tank filling level sensor 13 is provided, the measurement signal of which is representative of the filling level h of the fluid 9 in the fluid tank 7.

Furthermore, for example an ultrasound-based urea concentration sensor 17 is arranged on the feed line 15, the measurement signal of which urea concentration sensor 17 is representative of a propagation time of an ultrasonic pulse along a predefined path length in the fluid of the urea solution supply, that is to say in the fluid in the feed line 15 in the case of arrangement on the feed line 15. The urea concentration sensor 17 can also particularly advantageously be embodied as a structural unit with the tank filling level sensor 13. This is advantageous, in particular, when the tank filling level sensor 13 is also ultrasound-based. In this case, multiple use of the sensor can be achieved.

In addition, a heating unit 19 is preferably arranged in the feed line 15 or on the feed line 15. This may be provided, in particular, for the purpose of avoiding, during operation of the internal combustion engine, freezing of the fluid in the feed line or of making frozen fluid liquid again.

In addition, the ultrasound-based urea concentration sensor 17 can, in a structural unit, also optionally comprise a heating unit by which fluid that flows in the region of the ultrasound-based urea concentration sensor 17 can be correspondingly heated.

In addition, a control device 23 is provided that can also be referred to as a device for operating the SCR system, which control device 23 comprises a data memory and/or program memory and in addition comprises a processor and, in addition, also various inputs and outputs. The corresponding sensors are assigned to the inputs of the control device 23. Such sensors may be, for example, a temperature sensor 21, which is arranged in such a way that its measurement signal is representative of a temperature of the fluid 9, to be precise, in particular, in the range in which the ultrasound-based urea concentration sensor 17 is arranged. Furthermore, the tank filling level sensor 13 and/or the ultrasound-based urea concentration sensor 17 can be assigned to the control device 23 as sensors.

A program stored in the program memory of the control device 23 is processed during the operation of the SCR system, to be precise, in particular in the processor of the control device 23. Furthermore, various actuators, which can comprise, for example, the metering unit 3 and/or the tank heating element 11 and/or the heating unit 19, are assigned to the outputs of the control device 23. However, they can basically also comprise further actuators such as, for example, an injection valve for metering fuel.

A program is started, for example, close in terms of timing to starting of the internal combustion engine. The program can optionally check whether a predefined threshold value of the nitrogen oxide concentration in the exhaust gas downstream of the SCR catalytic converter 5 has been exceeded.

For this purpose, it is possible, for example, to use the measurement signal of the nitrogen oxide sensor 6. If this is the case, at least the fluid in a detection range of the urea concentration sensor 17 is thus heated from a predefined first temperature to a predefined second temperature. This can take place, depending on the arrangement of the ultrasound-based urea concentration sensor 17, by, for example, corresponding actuation of the heating unit in a structural unit with the ultrasound-based urea concentration sensor 17 and/or the heating unit 19 and/or the tank heating element 11.

During the heating, the measurement signal of the ultrasound-based urea concentration sensor 17 is detected at at least a third and a fourth temperature, and in each case a raw concentration characteristic value, representative of the propagation time of the ultrasonic pulse, is determined as a function of the respective measurement signal. It is therefore possible to determine at least two such raw concentration characteristic values and also any desired higher value. In particular in the case of the determination of merely two raw concentration characteristic values, it is particularly advantageous if the third and fourth temperatures correspond approximately to the first or second temperature. The raw concentration characteristic value may be, for example, the propagation time itself or, for example, a concentration value, that is to say, for example, as a percentage value.

A concentration characteristic value representative of a concentration of urea in the fluid is determined as a function of the raw concentration characteristic values.

This can take place optionally in that a gradient is determined as a function of the raw concentration characteristic values and the assigned temperatures, and the concentration characteristic value is determined as a function of the gradient.

It is particularly advantageous if the difference between the first and second temperatures is greater than a measuring inaccuracy of the ultrasound-based urea concentration sensor 17. This may be, for example, a temperature difference of at least 10° C.

Figure 2:
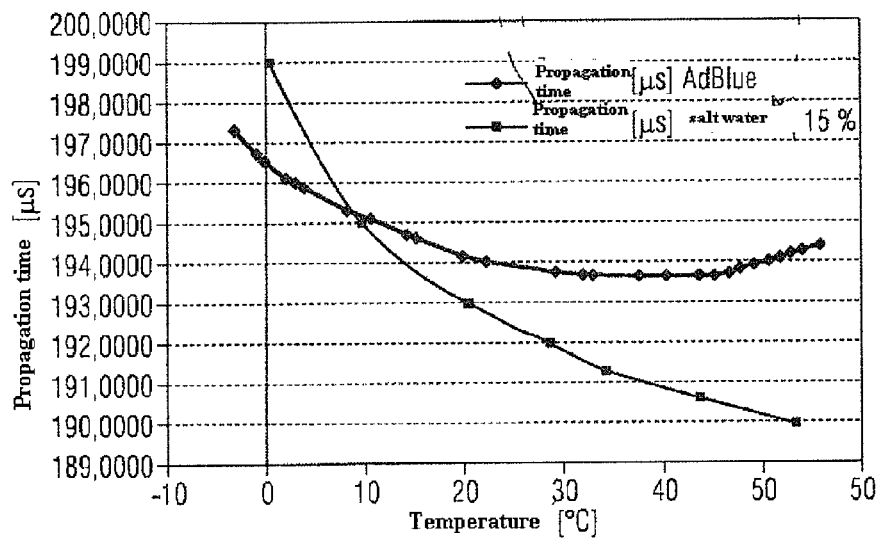
FIG. 2 shows profiles of raw concentration characteristic values plotted against the temperature.
Figure 3:
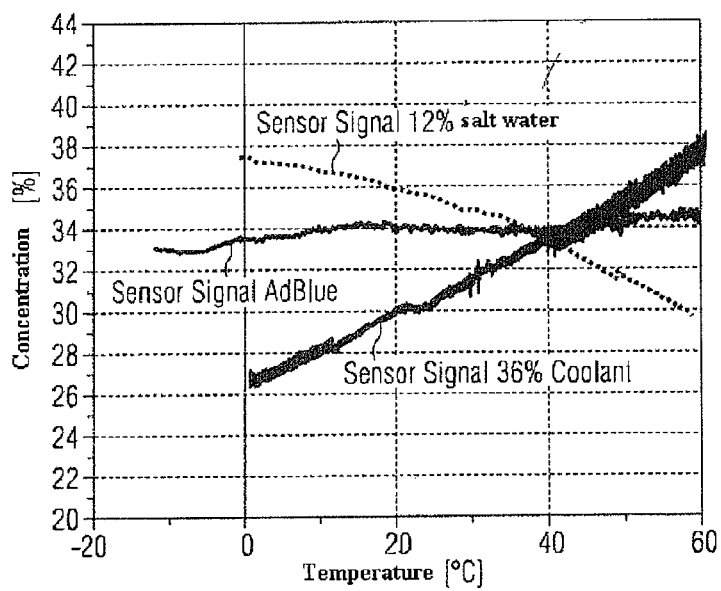
FIG. 3 shows further profiles of raw concentration characteristic values plotted against the temperature.

Profiles of the raw concentration characteristic value for various fluids are plotted against the temperature in FIGS. 2 and 3.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A selective catalytic reduction (SCR) system in an internal combustion engine, comprising:
   a urea solution supply;
   an ultrasound based urea concentration sensor (17) configured to produce a measurement signal representative of a propagation time of an ultrasonic pulse along a predefined path length in a fluid (9) of the urea solution supply;
   an SCR catalytic converter (5) in an exhaust gas duct (1);
   a feed line (15), configured to supply the fluid (9) to the exhaust gas duct (1) at a point upstream of the SCR catalytic converter (5);
   a dispenser (3) arranged upstream of the SCR catalytic converter (5) and configured to dispense an amount of the fluid (9) entering the exhaust gas duct (1);
   a nitrogen sensor (6) arranged downstream of the SCR catalytic converter (5) in the exhaust gas duct (1), and a control device (23); and
   the control device being configured to, if a detection by the nitrogen sensor (6) indicates that the nitrogen oxide concentration in exhaust gas downstream of the SCR catalytic converter (5) exceeds a predefined threshold value:
   heat at least the fluid (9) in a detection region of the urea concentration sensor (17) from a predefined first temperature to a predefined second temperature;
   detect the measurement signal during the heating at at least a third and fourth temperature and in each case to determine a raw concentration characteristic value, as a function of the respective measurement signal, which raw concentration characteristic value is representative of the propagation time of the ultrasonic pulse; and
   determine a concentration characteristic value, representative of a concentration of urea in the fluid (9), as a function of the raw concentration characteristic values by:
      determining a gradient as a function of the raw concentration characteristic values and the assigned temperatures, and
      determining the concentration characteristic value as a function of the gradient; and
   on the basis of the determined concentration characteristic, adjusting the dispensed quantity of the fluid (9) being provided to the exhaust gas duct (1).

2. A method on a selective catalytic reduction (SCR) system for an internal combustion engine, the selective catalytic reduction (SCR) system having: a urea solution supply, an ultrasound based urea concentration sensor (17) configured to produce a measurement signal representative of a propagation time of an ultrasonic pulse along a predefined path length in a fluid (9) of the urea solution supply, an SCR catalytic converter (5) in an exhaust gas duct (1), a feed line (15), configured to supply the fluid (9) to the exhaust gas duct (1) at a point upstream of the SCR catalytic converter (5), a dispenser (3) arranged upstream of the SCR catalytic converter (5) and configured to dispense an amount of the fluid (9) entering the exhaust gas duct (1), a nitrogen sensor (6) arranged downstream of the SCR catalytic converter (5) in the exhaust gas duct (1), and a control device (23), the method comprising:
   detection, by the nitrogen sensor (6), whether the nitrogen oxide concentration in exhaust gas downstream of the SCR catalytic converter (5) exceeds a predefined threshold value, and if the nitrogen oxide concentration exceeds the predefined threshold value, performing the following steps:
   heating at least the fluid (9) in a detection region of the urea concentration sensor (17) from a predefined first temperature to a predefined second temperature;
   during the heating, the control device (23) detecting the measurement signal at at least a third and fourth temperature, and in each case determining a raw concentration characteristic value as a function of the respective measurement signal;
   determining a concentration characteristic value, representative of a concentration of urea in the fluid (9), as a function of the raw concentration characteristic values by:
      determining a gradient as a function of the raw concentration characteristic values and the assigned temperatures, and determining the concentration characteristic value as a function of the gradient; and on the basis of the determined concentration characteristic, adjusting the dispensed quantity of the fluid (9) being provided to the exhaust gas duct (1).

3. The method as claimed in claim 2, wherein the urea concentration sensor (17) is configured to detect a fluid filling level in a fluid tank (7) of the urea solution supply (5).

4. The method as claimed in claim 2, wherein the difference between the first and second temperatures is greater than a measuring inaccuracy of the urea concentration sensor (17).

5. The method as claimed in claim 2, wherein the difference between the first and second temperatures is at least 10° C.

6. The method as claimed in claim 2, wherein the urea concentration sensor (17) is configured to emit the ultrasonic pulse into a feed line (15) of the urea solution supply.

* * * * *